US00PP12191P2

(12) United States Plant Patent
Glicenstein

(10) Patent No.: US PP12,191 P2
(45) Date of Patent: Nov. 6, 2001

(54) CARNATION PLANT NAMED 'CANTARE'

(75) Inventor: Leon Glicenstein, Lebanon, IN (US)

(73) Assignee: Yoder Brothers, Inc., Barberton, OH (US)

( * ) Notice: Subject to any disclaimer, the term of this patent is extended or adjusted under 35 U.S.C. 154(b) by 0 days.

(21) Appl. No.: 09/748,694

(22) Filed: Dec. 27, 2000

(51) Int. Cl.[7] ..... A01H 5/00
(52) U.S. Cl. ..... Plt./274

(58) Field of Search ..... Plt./274

*Primary Examiner*—Bruce R. Campell
*Assistant Examiner*—Kent L. Bell
(74) *Attorney, Agent, or Firm*—C. A. Whealy

(57) ABSTRACT

A distinct cultivar of Carnation plant named 'Cantare', characterized by its white-colored flowers; early and freely flowering habit; fragrant flowers; good postproduction longevity with flowers maintaining good substance and color for more than two weeks in an interior environment; and resistance to *Fusarium oxysporum*.

2 Drawing Sheets

BACKGROUND OF THE INVENTION

The present invention relates to a new and distinct cultivar of Carnation plant, botanically known as *Dianthus caryophyllus* and hereinafter referred to by the name 'Cantare'.

The new Carnation is a product of a planned breeding program conducted by the Inventor in Salinas, Calif. The objective of the breeding program is to create new cut Carnation cultivars having long flowering stems, early flowering, attractive flower color, and good flower form and substance.

The new Carnation originated from a cross made by the Inventor in 1991, in Salinas, Calif., of the carnation cultivar 'Lek's White Pirouette', not patented, as the male, or pollen, parent with a proprietary Carnation seedling selection identified as code number 1462, as the female, or seed, parent.

The cultivar 'Cantare' was discovered and selected by the Inventor as a flowering plant within the progeny of the stated cross in a controlled environment in Suba, Cundinamarca, Colombia, in October, 1991. The selection of this plant was based on its flower color and good flower form and substance.

Asexual reproduction of the new Carnation by terminal cuttings taken in a controlled environment in Suba, Cundinamarca, Colombia, has shown that the unique features of this new Carnation are stable and reproduced true to type in successive generations.

SUMMARY OF THE INVENTION

The cultivar 'Cantare' has not been observed under all possible environmental conditions. The phenotype may vary somewhat with variations in environment such as temperature, daylength, light intensity, and water and nutritional status without, however, any variance in genotype.

The following traits have been repeatedly observed and are determined to be the unique characteristics of 'Cantare'. These characteristics in combination distinguish 'Cantare' as a new and distinct cultivar:

1. Pure white-colored flowers.

2. Early and freely flowering habit with about 10 to 12 flowers per flowering stem.

3. Fragrant flowers.

4. Good postproduction longevity with flowers maintaining good substance and color for more than two weeks in an interior environment.

5. Resistance to *Fusarium oxysporum.*

Plants of the new Carnation differ primarily from plants of the parent plants in flower form and substance.

Plants of the new Carnation can be compared to plants of the cultivar 'Bagatel', disclosed in U.S. Plant Pat. No. 6,600. In side-by-side comparisons conducted in Suba, Cundinamarca, Colombia, plants of the new Carnation and the cultivar 'Bagatel' differ in the following characteristics:

1. Plants of the new Carnation have longer, stronger and thicker flowering stems than plants of the cultivar 'Bagatel'.

2. Plants of the new Carnation flower about three weeks earlier than plants of the cultivar 'Bagatel'.

3. Flower spray formation of plants of the new Carnation is more open than flower spray formation of plants of the cultivar 'Bagatel'.

4. When opening, flowers of plants of the new Carnation are whiter in color than flowers of plants of the cultivar 'Bagatel'.

5. Flowers of plants of the new Carnation have more petals and petaloids and appear fuller than flowers of plants of the cultivar 'Bagatel'.

6. Petal margins of plants of the new Carnation are more fringed than petal margins of plants of the cultivar 'Bagatel'.

7. Flowers of plants of the new Carnation are slightly less fragrant than flowers of plants of the cultivar 'Bagatel'.

BRIEF DESCRIPTION OF THE PHOTOGRAPHS

The accompanying colored photographs illustrate the overall appearance of the new Carnation, showing the colors as true as it is reasonably possible to obtain in colored reproductions of this type. Colors in the photographs may differ slightly from the color values cited in the detailed botanical description which accurately describe the colors of the new Carnation.

The photograph on the first sheet comprises a side perspective view of a typical flowering stem of 'Cantare' grown as a spray-type cut Carnation.

The photograph at the top of the second sheet comprises a close-up view of typical flowers of 'Cantare'.

The photograph at the bottom of the second sheet comprises a close-up view of typical flowers of 'Cantare' (left) and 'Bagatel' (right).

DETAILED BOTANICAL DESCRIPTION

In the following description, color references are made to The Royal Horticultural Society Colour Chart except where general terms of ordinary dictionary significance are used. The following observations and measurements describe plants grown in Madrid, Cundinamarca, Colombia, under conditions which approximate commercial practice in a single-layer polyethylene-covered greenhouse. Four-week old rooted cuttings were planted in ground beds and pinched about 3 to 4 weeks later. During the production time, the following environmental conditions were measured: day temperatures, 19 to 24° C.; night temperatures, 4 to 12° C.; and light levels, about 3,000 to 5,000 foot-candles. Measurements and numerical values represent averages for six to ten typical flowering stems that were harvested from plants that were about 24 to 26 weeks after planting.

Botanical classification: *Dianthus caryophyllus* cultivar 'Cantare'.

Commercial classification: Miniature spray-type cut Carnation.

Parentage:

*Male or pollen parent.*—*Dianthus caryophyllus* cultivar 'Lek's White Pirouette', not patented.

*Female or seed parent.*—Proprietary *Dianthus caryophyllus* seedling selection identified as code number 1462, not patented.

Propagation:

*Type.*—Terminal tip cuttings.

*Time from sticking unrooted cuttings to planting.*—About 4 weeks.

*Root description.*—Fine, freely-branching.

Plant description:

*Flowering stem description.*—Aspect: Mostly upright. Strength: Strong, flexible. Length: About 90.2 cm. Diameter: About 3 mm. Internode length, between $4^{th}$ and $5^{th}$ node: About 8.5 cm. Texture: Smooth. Color: Darker than 147A, overlain with waxy bloom, close to 188A.

*Foliage description.*—Arrangement: Opposite; sessile. Aspect: Slightly concave; reflexed. Length: About 13.6 cm. Width: About 7.5 mm. Shape: Linear. Apex: Sharply acute. Margin: Entire. Texture: Tough, leathery; waxy. Color: Young foliage, upper and lower surfaces: Slightly darker than 147A, overlain with waxy bloom, close to 188A. Mature foliage, upper and lower surfaces: Slightly darker than 147A, overlain with waxy bloom, close to 188A.

Flowering description:

*Appearance.*—Single flowers arranged in sprays. Freely flowering, usually about 10 to 12 flowers per flowering stem.

*Flowering season response.*—Year-round under greenhouse conditions; plants flower about 24 weeks after planting rooted cuttings.

*Postproduction longevity.*—In an interior environment, flowering stems will maintain good color and substance for more than two weeks. Flowers persistent.

*Fragrance.*—Moderately fragrant; spicy, clove-like.

*Flower size.*—Diameter: About 5.4 cm. Depth (height): About 2.5 cm.

*Flower buds* (*at stage of showing color*).—Length: About 2.5 cm. Diameter: About 1.1 cm. Shape: Oblong. Color: White, close to 155D.

*Petals/petaloids.*—Quantity: About 36, imbricate. Length: About 4.7 cm. Width: About 2.5 cm. Shape: Roughly spatulate. Apex: Rounded. Base: Attenuate to acute. Margin: Finely serrated giving a fringed appearance. Texture: Satiny, smooth, glabrous. Color: When opening, upper and lower surfaces: White, 155D, iridescent. Fully opened, upper and lower surfaces: White, 155D; iridescent.

*Sepals.*—Quantity: About 5 or 6, fused. Length: About 2.4 cm. Width: About 8 mm. Calyx diameter: Apex: About 1.3 cm. Base: About 1 cm. Shape: Roughly ovate. Apex: Sharply acute. Texture: Tough, leathery; smooth; waxy, longitudinally ridged. Resistance to splitting: Good, calyxes rarely split. Color: Upper surface: Close to 157A. Lower surface: 146A, towards base lighter than 146A.

*Reproductive organs.*—Androecium: Stamen number: About 6. Stamen length: About 1.4 cm. Stamen color: White, close to 155D. Anther size: About 2.5 mm by 1 mm. Anther shape: Oblong. Anther color: White, close to 155D. Pollen: None observed. Gynoecium: Pistil quantity: Three, fused. Pistil length: About 3.6 cm. Pitsil color: White, close to 155D. Receptacle size: About 9 mm by 6 mm. Receptacle color: 144A.

*Seed.*—Seed production has not been observed.

Disease resistance: Plants of the new Carnation planted in soils heavily infested with *Fusarium oxysporum* have been observed to be highly resistant to *Fusarium oxysporum.*

It is claimed:

1. A new and distinct cultivar of Carnation plant named 'Cantare', as illustrated and described.

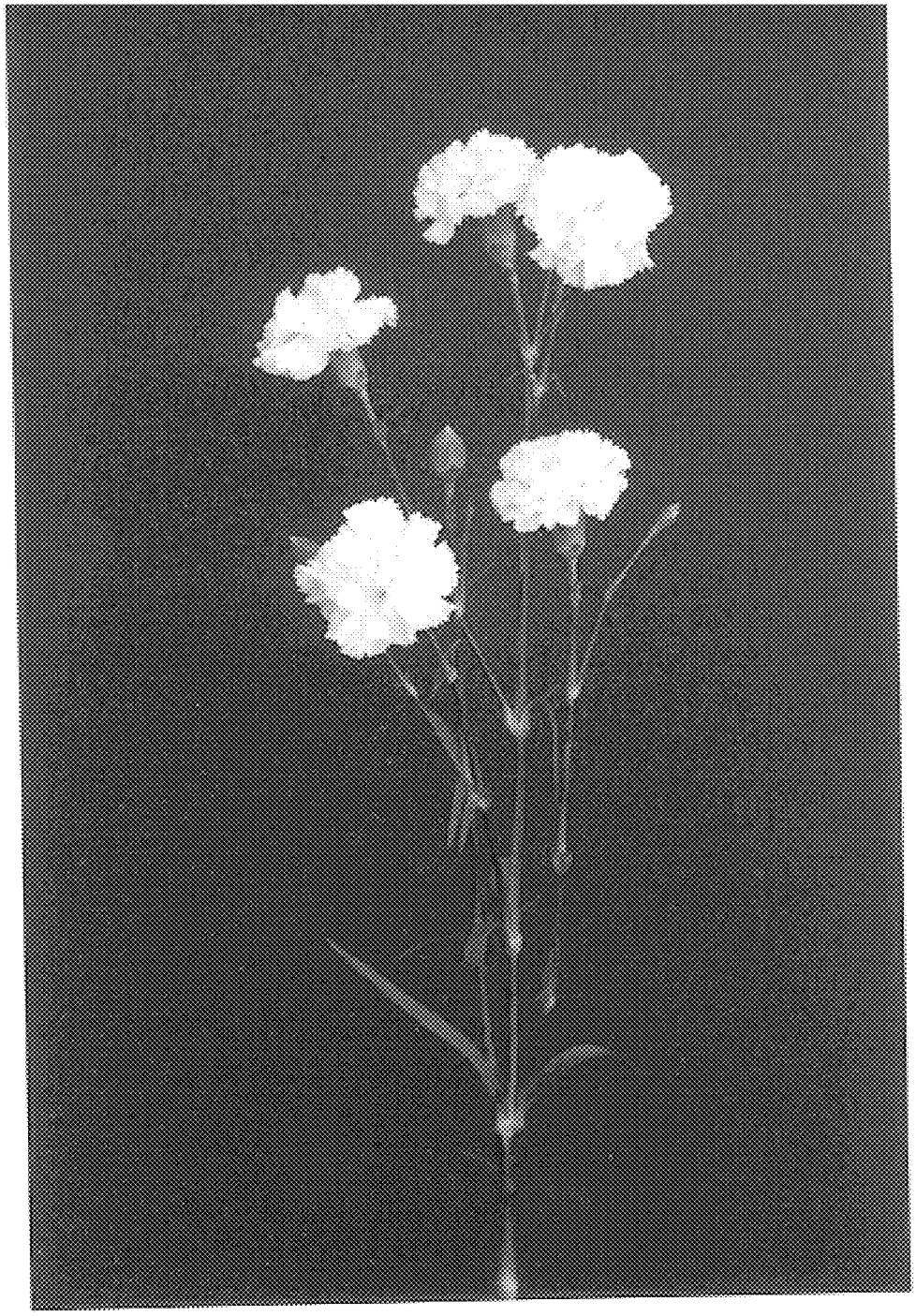

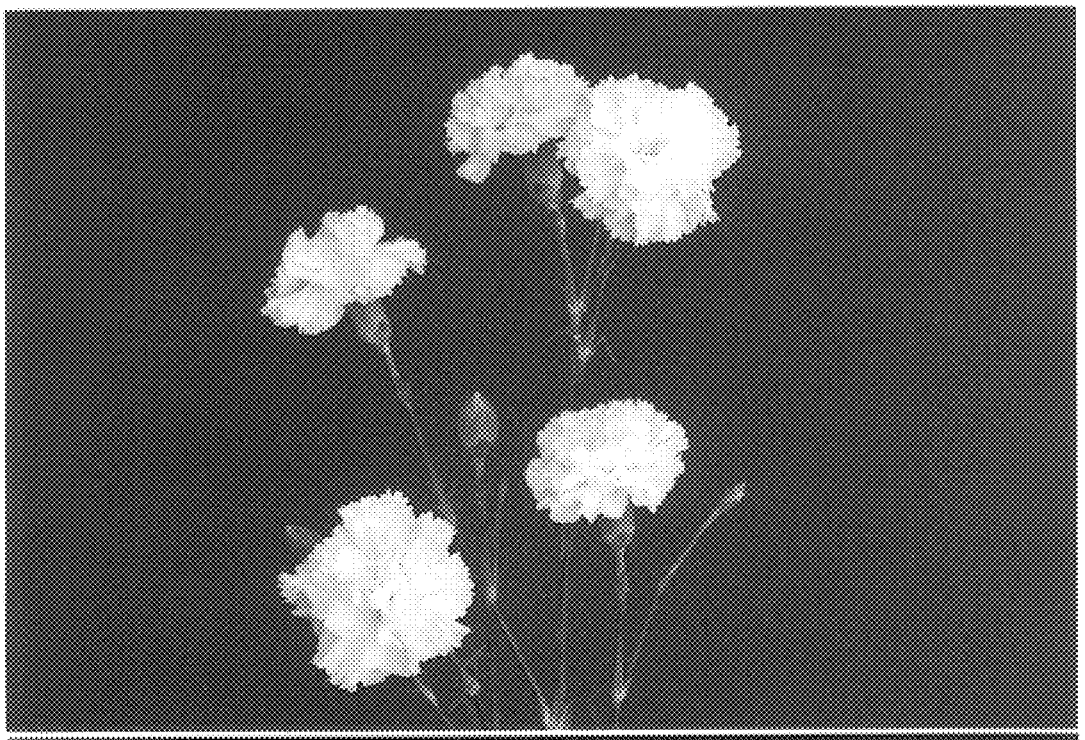
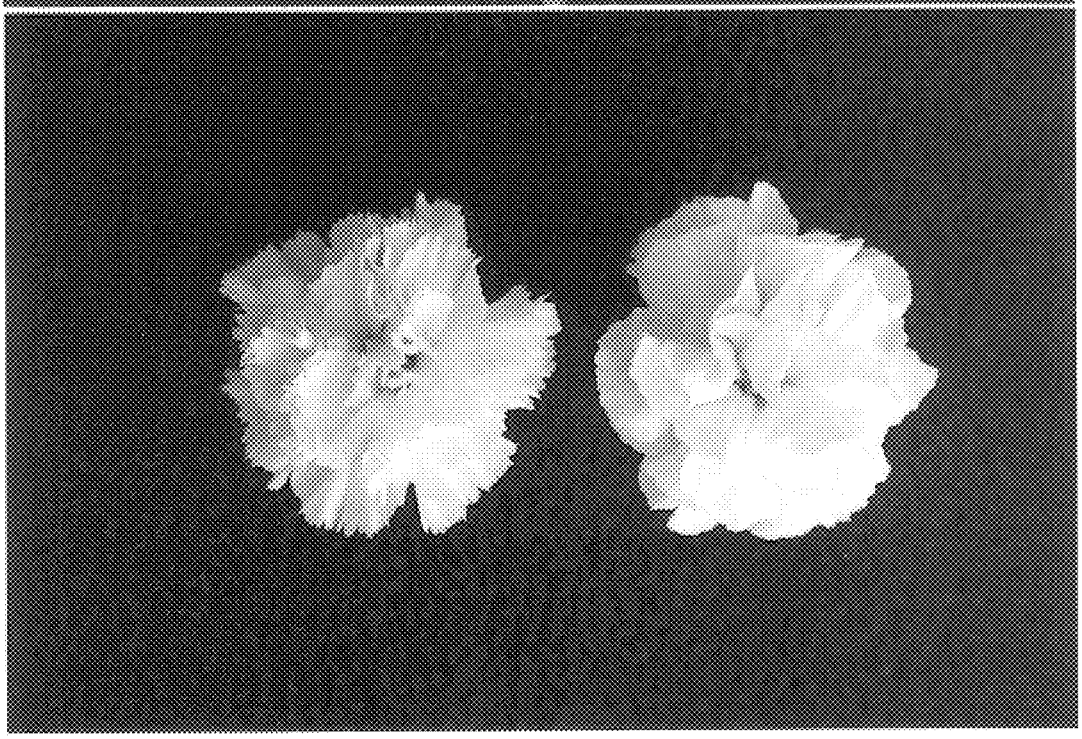

* * * * *